US006498138B1

(12) United States Patent
Rodgers et al.

(10) Patent No.: US 6,498,138 B1
(45) Date of Patent: Dec. 24, 2002

(54) METHOD OF PROMOTING PRODUCTION OF LIVING TISSUE EQUIVALENTS

(75) Inventors: Kathleen E. Rodgers, Long Beach; Gere DiZerega, Pasadena, both of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/266,293

(22) Filed: Mar. 11, 1999

Related U.S. Application Data

(60) Provisional application No. 60/077,499, filed on Mar. 11, 1998, and provisional application No. 60/089,064, filed on Jun. 12, 1998.

(51) Int. Cl.⁷ ............................................. A01N 37/18
(52) U.S. Cl. ............................................. 514/2; 514/2
(58) Field of Search .................. 530/350, 300; 514/2, 21

(56) References Cited

U.S. PATENT DOCUMENTS

| | | | |
|---|---|---|---|
| 4,485,096 A | 11/1984 | Bell | 424/95 |
| 4,485,097 A | 11/1984 | Bell | 424/95 |
| 4,539,716 A | 9/1985 | Bell | 623/1 |
| 4,546,500 A | 10/1985 | Bell | 623/1 |
| 4,604,346 A | 8/1986 | Bell et al. | 435/1 |
| 4,835,102 A | 5/1989 | Bell et al. | 435/29 |
| 4,837,379 A | 6/1989 | Weinberg | 424/101 |
| 5,015,629 A | 5/1991 | diZerega | 514/16 |
| 5,052,934 A | 10/1991 | Carey et al. | 434/268 |
| 5,192,312 A | 3/1993 | Orton | 623/2 |
| 5,256,418 A | 10/1993 | Kemp et al. | 424/423 |
| 5,387,236 A | 2/1995 | Noishiki et al. | 623/1 |
| 5,478,739 A | 12/1995 | Slivka et al. | 435/240.23 |
| 5,480,424 A | 1/1996 | Cox | 623/2 |
| 5,510,254 A | 4/1996 | Naugton et al. | 435/240.243 |
| 5,512,475 A | 4/1996 | Naughton et al. | 435/240.243 |
| 5,516,680 A | 5/1996 | Naughton et al. | 435/240.243 |
| 5,516,681 A | 5/1996 | Naughton et al. | 435/240.243 |
| 5,521,087 A | 5/1996 | Lee et al. | 435/240.2 |
| 5,536,656 A | 7/1996 | Kemp et al. | 435/240.23 |
| 5,541,107 A | 7/1996 | Naughton et al. | 435/240.23 |
| 5,578,485 A | 11/1996 | Naughton et al. | 435/240.23 |
| RE35,399 E | 12/1996 | Eisenberg | 623/11 |
| 5,624,840 A | 4/1997 | Naughton et al. | 435/240.23 |
| 5,628,781 A | 5/1997 | Williams et al. | 623/1 |
| 5,629,292 A | 5/1997 | Rodgers et al. | 514/16 |
| 5,693,616 A | 12/1997 | Krstenansky et al. | 514/12 |
| 5,712,163 A | 1/1998 | Parenteau et al. | 435/405 |
| 5,713,950 A | 2/1998 | Cox et al. | 623/2 |
| 5,716,935 A | 2/1998 | Rodgers et al. | 514/16 |
| 5,834,432 A | 11/1998 | Rodgers et al. | 514/16 |
| 5,955,430 A | 9/1999 | Rodgers et al. | 514/16 |

FOREIGN PATENT DOCUMENTS

| | | |
|---|---|---|
| WO | WO 95/08337 | 3/1995 |
| WO | WO 95/08565 | 3/1995 |
| WO | WO 96/14858 * | 5/1996 |
| WO | WO 96/15795 | 5/1996 |
| WO | WO 96/39164 | 12/1996 |
| WO | WO 96/40090 | 12/1996 |
| WO | WO 98/26795 | 6/1998 |
| WO | WO 98/32457 | 7/1998 |
| WO | WO 98/33813 | 8/1998 |

OTHER PUBLICATIONS

Ahern, The Scientist Library, pp. 1–5, 1995.*
Catalioto, R.–M., et al., *European J. of Pharmacology*, 256: pp. 93–97 (1994).
Kageyama, R., et al., *Biochemistry*, 23: pp. 3603.
Kauffman, R.F., et al., *Pharmacology Lett.*, 49(25): pp. 223.
Ohkubo, H., et al., *Biochemistry*, 80: pp. 2196.
Rodgers K., et al., *J. Burn Care & Rehab.*, 18(5): pp. 381.
Stouffer, G.A. and Owens, G.K., *Circulation Res.*, 70: pp. 820.
Wolf, F., et al., *Am. J. Pathology*, 140(1): pp. 95.
Satya P. Kunapuli, and Ashok Kumar, "Molecular Cloning of Human Angiotensinogen cDNA and Evidence for the Presence of Its mRNA in Rat Heart," *Circulation Research*, vol. 60 (1987) pp. 786–790.
Richard M. Edwards and Elwood J. Stack, "Angiotensin II Inhibits Glomerular Adenylate Cyclase via the Angiotensin II Receptor Subtype 1 ($AT_1$)," *The Journal of Pharmacology and Experimental Therapeutics*, vol. 266, No. 2 (1993), pp. 506–510.
Margaret Forney Prescott, Randy L. Webb and Michael A Reidy, "Angiotensin–Converting Enzyme Inhibitor Versus Angiotensin II, $AT_1$ Receptor Antagonist," *American Journal of Pathology*, vol. 139, No. 6 (1991) pp. 1291–1296.
Sadoutounissa Shanmugam, Catherine Llorens–Cortes, Eric Clauser, Pierre Corvol and Jean–Marie Gasc, "Expression of Angiotensin II $AT_2$ Receptor mRNA During Development of Rat Kidney and Adrenal Gland," *The American Physiological Society* (1995) pp. F922–F930.
Leonardo A Fernandez, Jeff Twickler, and Alden Mead, "Neovascularization Produced by Angiotensin II," *The Journal of Laboratory and Clinical Medicine*, vol. 105, No. 2 (1985) pp. 141–145.
Karri Helin, Monika Stoll, Simone Meffert, Ursula Stroth, and Thomas Unger, "The Role of Angiotensin Receptors in Cardiovascular Diseases," *Annals of Medicine*, vol. 29 (1997) pp. 23–29.

(List continued on next page.)

*Primary Examiner*—Karen Cochrane Carlson
*Assistant Examiner*—Hope Robinson
(74) *Attorney, Agent, or Firm*—McDonnell Boehnen Hulbert & Berghoff; David S. Harper

(57) ABSTRACT

The present invention provides methods, improved cell culture medium and kits for accelerating the generation of tissue equivalents, and for improving the quality of tissue equivalents, by growth in the presence of angiotensinogen, AI, AI analogues, AI fragments and analogues thereof, AII, AI analogues, AII fragments and analogues thereof and/or AII $AT_2$ type 2 receptor agonists.

22 Claims, No Drawings

OTHER PUBLICATIONS

Neelam Jaiswal, E Ann Tallant, Rama K. Jaiswal, Debra I. Diz, Carlos M. Ferrario: "Differential Regulation of Prostaglandin Synthesis by Angiotensin Peptides in Porcine Aortic Smooth Muscle Cells: Subtypes of Angiotensin Receptors Involved," *The Journal of Pharmacology and Experimental Therapeutics*, vol. 265, No. 2. (1991) pp. 664–673.

Neelam Jaiswal, E Ann Tallant, Debra I. Diz Mahesh C. Khosla Carlos M. Ferrario, "Subtype 2 Angiotensin Receptors Mediat Prostaglandin Synthesis in Human Astrocytes," *Hypertension*, vol. 17 (1991) pp. 1115–1120.

Neelam Jaiswal, Debra I. Diz, Mark C. Chappell, Mahesh C. Khosla, and Carlos M. Ferrario, "Stimulation of Endolthelial Cell Prostaglandin Production by Angiotensin Peptides; Characterization of Receptors," *Hypertension*,(1992) vol. 19[suppl II]:II–49–II–55).

Philip Janiak, Aline Pillon, Jean–Francois Prost, and Jean–Paul Vilaine, "Role of Angiotensin Subtype 2 Receptor in Neointima Formation After Vascular Injury," *Hypertension*, vol. 20 (1992) pp. 737–745.

Birgitta Kimura, Colin Sumners and M. Ian Phillips, "Changes in Skin Angiotensin II Receptors in Rats During wound Healing," *Biochemical and Biophysical Research Communications*, vol. 187, No. 2 (1992) pp. 1083–1090.

Yasuhiro Kawahara, Michitoshi Sunako, Terutaka Tsuda, Hisashi Fukuzaki, Yasuo Fukumoto and Yoshimi Takai, "Angiotensin II Induces Expression of the C–Fos Gene Through Protein Kinase C Activation and Calcium Ion Mobilization In Cultured Vascular Smooth Muscle Cells," *Biochemical and Biophysical Research Communications*, vol. 150. No. 1 (1988) pp. 52–59.

Ferdinand A.C. Le Noble, Johan W. M. Hekking, Henny W. M. Van Straaten, Dick W. Slaaf and Harry A.J. Struyker Boudier, "Angiotensin II Stimulates Angiogenesis in the Chorio–Allantoic Membrane of the Chick Embryo," *Euopean Journal of Pharmacology*, vol. 195 (1991) pp. 305–306.

Allen J. Naftilan, Richard E. Pratt, and Victor J. Dzau, " Induction of Patelet–Derived Growth Factor A–Chain and C–myc Gene Expressions by Angiotensin II in Cultured Rat Vascular Smooth Muscle Cells," *J. Clin. Inest.*, vol. 83, (1989) pp. 1419–1424.

Victor E. Dzau, Richard Pratt, Gary Gibbons, Heribert Schunkert, Beverly Lorell, and Julie Ingelfinger, "Molecular Mechanism of Angiotensin in the Regulation of Vascular and Cardiac Growth," *Journal of Molecular Cell Cardiology*, vol. 21 (Supplement III) (1989) p. S.7.

Ken–ichi Nakahara, Hiroshi Nishimura, Makoto Kuro–o, Shun–ichi Takewaki, Misaki Iwase1, Akiyuki Ohkubo, Yosio Yazaki and Ryozo Nagai1. "Identification of Three Types of PDGF–A Chain Gene Transcripts in Rabbit Vascular Smooth Muscle and Their Regulated Expression During Development and by Angiotensin II," *Biochemical and Biophysical Research Communication*, vol. 184, No. 2 (1992) pp. 811–818.

Ilkka Porsti, Agnieszka T. Bara, Rudi Busse and Markus Hecker, "Release of Nitric Oxide by Angiotensin–(1–7) From Porcine Coronary Endothelium: Implications for a Novel Angiotensin Receptor," *Br. J. Pharmacol*, vol. 111 (1994) pp. 652–654.

Josef Pfeilschifter, Andrea Huwiler, Claire Merriweather and Vreny A. Briner, "Angiotensin II Stimulation of Phospholipase D in Rat Renal Mesangial Cells is Mediated by the $AT_1$ Receptor Subtype," *European Journal of Pharmacology–Molecular Pharmacology* Section, vol. 225 (1992) pp. 57–62.

Katania Bedecs, Nathalie Elbaz, Malene Sutren, Maryline Masson, Christiane Susini†, A. Donny Strosberg and Clara Nahmias, "Angiotensin II Type 2 Receptors Mediate Inhibition of Mitogen–Activated Protein Kinase Cascade and Functional Activation of SHP–1 Tyrosine Phosphatase," *Biochem. J.* vol. 325 (1997) pp. 449–454.

Leonard Bell and Joseph A. Madri, "Influence of the Angiotensin System on Endothelial and Smooth Muscle Cell Migration," *American Journal of Pathology*, vol. 137, No. 1. (1990) pp. 7–12.

Bradford C. Berk, Vladimir Vekshtein, Helen M. Gordon, Terutaka Tsuda "Angiotensin II–Stimulated Protein Synthesid in Cultured Vascular Smooth Muscle Cells," *Hypertension*, vol. 13, (1989) pp. 305–314.

W.M. Clouston, B.A. Evans, J. Haralambidis, and R.I. Richards, "Molecular Cloning of the Mouse Angiotensinogen Gene," *Genomics*, vol. 2 (1988) pp. 240–248.

Susan E. Bryson, Philip Warburton, Helen P. Wintergill, G. Michael Drew, Anton D. Michel, Stephen G. Ball and Anthony J. Balmforh, "Induction of the Angiotensin AT2 Receptor Subtype Expression by Differentiation of the Neuroblastoma X Glioma Hybrid, NG–108–15," *European Journal of Pharmacology*, vol. 225 (1992) pp. 119–127.

Kathleen E. Rodgers, Alexander H. DeCherney, Karen M. St. Amand, William R. Dougherty, Juan C. Felix, Wefki W. Girgis and Gere S. diZerega, "Histologic Alterations in Dermal Repair After Thermal Injury Effects of Topical Angiotensin II," *J. Burn Care Rehabilitation*, vol. 18 (1997) pp. 381–388.

D. Regoli, W. K. Park and F. Rioux, "Pharmacology of Angiotensin" *Pharmacological Review*, vol. 26, No. 2 (1989) pp. 69–119.

Robert C. Speth, and Kwan Hee Kim, "Discrimination of Two Angiotensin II Receptor Subtypes with a Selective Agonist Analogue of Angiotensin II,p–Aminophenylalanine Angiotensin II," *Biochemical and Biophysical Research Communications*, vol. 169, No. 3 (1990) pp. 997–1006.

Mark B. Taubman, Bradford C. Berk, Seigo Izumo, Terutaka Tsuda, R. Wayne Alexander, and Bernardo Nadal–Ginard, "Angiotensin II Induces c–fos mRNA in Aortic Smooth Muscle," *The Journal of Biological Chemistry*, vol. 264, No. 1 (1989) pp. 526–530.

Mohan Viswanathan1 and Juan M. Saavedra: "Expression of Angiotensin II $AT_2$ Receptors in the Rat Skin During Experimental Wound Healing," *Peptides*, vol. 13 (1992) pp. 783–786.

* cited by examiner

SEQUENCE LISTING

<160> NUMBER OF SEQ ID NOS: 42

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
 1               5

```
<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
 1

<210> SEQ ID NO 8
```

<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8

Asp Arg Val Tyr Ile His
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

Asp Arg Val Tyr
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
 1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<221> NAME/KEY: MOD_RES
<222> LOCATION: (2)
<223> OTHER INFORMATION: Nle

<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<221> NAME/KEY: MOD_RES
<222> LOCATION: (4)
<223> OTHER INFORMATION: Nle

<400> SEQUENCE: 13

```
Arg Val Tyr Xaa His Pro Phe
 1               5
```

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

```
His Pro Phe
 1
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

```
Tyr Ile His Pro Phe
 1               5
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<221> NAME/KEY: UNSURE
<222> LOCATION: (1)
<223> OTHER INFORMATION: Xaa at position 1 can be Arg, Lys, Ala, Orn,
      Ser(Acetylated), MeGly, D-Arg, or D-Lys
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

```
Xaa Xaa Tyr Xaa His Pro Phe
 1               5
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

```
Arg Val Tyr Gly His Pro Phe
 1               5
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

```
Arg Val Tyr Ala His Pro Phe
```

-continued

```
                 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
  1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue
      3

<400> SEQUENCE: 21

Ala Pro Gly Asp Arg Ile Tyr Val His Pro Phe
  1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII analogue
```

6

<400> SEQUENCE: 24

Asp Arg Ala Tyr Ile His Pro Phe
  1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue
      7

<400> SEQUENCE: 25

Asp Arg Val Thr Ile His Pro Phe
  1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue
      8

<400> SEQUENCE: 26

Asp Arg Val Tyr Leu His Pro Phe
  1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
      10

<400> SEQUENCE: 28

Asp Arg Val Tyr Ile His Ala Phe
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
  1               5

<210> SEQ ID NO 30

```
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
      14
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<221> NAME/KEY: MOD_RES
<222> LOCATION: (3)
<223> OTHER INFORMATION: Nle

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<221> NAME/KEY: MOD_RES
<222> LOCATION: (5)
<223> OTHER INFORMATION: Nle

<400> SEQUENCE: 34

Asp Arg Val Tyr Xaa His Pro Phe
 1               5

<210> SEQ ID NO 35
```

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence:
      p-aminophenylalanine 6 AII
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:
      angiotensin I

<400> SEQUENCE: 37

Asp Arg Val Tyr Ile His Pro Phe His Leu
 1               5                  10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:1GD:Ile8-AII

<400> SEQUENCE: 38

Asp Arg Val Tyr Ile His Pro Ile
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:Gly1-AII

<400> SEQUENCE: 39

Gly Arg Val Tyr Ile His Pro Phe
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:norLeu4-AIII

```
<221> NAME/KEY: MOD_RES
<222> LOCATION: (4)
<223> OTHER INFORMATION: Nle

<400> SEQUENCE: 40

Arg Val Tyr Xaa His Pro Phe
 1               5

<210> SEQ ID NO 41
<211> LENGTH: 8
<212> TYPE: PRT
<213> ORGANISM: Artificial Sequence
<220> FEATURE:
<221> NAME/KEY: MOD_RES
<222> LOCATION: (3)
<223> OTHER INFORMATION: Xaa at position 3 is 1-aminocyclopentane
      carboxylic acid
<223> OTHER INFORMATION: Description of Artificial Sequence:Acpc3-AII

<400> SEQUENCE: 41

Asp Arg Xaa Tyr Ile His Pro Phe
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence:2GD:
      Pro3-AII(1-7)

<400> SEQUENCE: 42

Asp Arg Pro Tyr Ile His Pro
 1               5
```

METHOD OF PROMOTING PRODUCTION OF LIVING TISSUE EQUIVALENTS

CROSS REFERENCE

This application is a continuation in part of U.S. application Ser. Nos. 60/077,499 filed Mar. 11, 1998 and 60/089,064 filed Jun. 12, 1998.

FIELD OF THE INVENTION

This present invention relates to methods, tissue culture medium, and kits for accelerating the production living tissue equivalents.

BACKGROUND OF THE INVENTION

Recently, various systems for the in vitro production of tissue equivalents have been described. As used herein, the term "tissue" comprises any group or layer of cells which together perform one or more certain functions. Such tissue equivalents include, but are not limited to, equivalents of epithelial tissue, connective tissue, cartilage, bone, organs, vascular grafts, glands and blood vessels and comprise living cells and extracellular matrix molecules, principally collagen, and may optionally be provided with components not typically found in normal tissue.

Three-dimensional cell culture systems have been described which can be used to culture a variety of different cells and tissues in vitro for prolonged periods of time (U.S. Pat. Nos. 5,624,840; 5,541,107; 5,521,087; 5,516,681, 5,516,680; 5,512,475, herein incorporated by reference in their entirety). Cells derived from a desired tissue are inoculated and grown on a pre-established stromal support matrix. The stromal support matrix comprises stromal cells, such as fibroblasts, actively growing on a three-dimensional matrix. Stromal cells may also include other cells found in loose connective tissue such as endothelial cells, macrophages/monocytes, adipocytes, pericytes, reticular cells found in bone marrow stroma, etc. The stromal matrix provides the support, growth factors, and regulatory factors necessary to sustain long-term active proliferation of cells in culture. When grown in this three-dimensional system, the proliferating cells mature and segregate properly to form components of adult tissues analogous to counterparts found in vivo.

These inventions are based, in part, on the discovery that growth of stromal cells in three dimensions will sustain active proliferation of cells in culture for longer periods of time than will monolayer systems (U.S. Pat. No. 5,510,254). This may be due, in part, to the increased surface area of the three-dimensional matrix which results in a prolonged period of active proliferation of stromal cells. These proliferating stromal cells elaborate proteins, growth factors and regulatory factors necessary to support the long term proliferation of both stromal and tissue-specific cells inoculated onto the stromal matrix. In addition, the three-dimensionality of the matrix allows for a spatial distribution which more closely approximates conditions in vivo, thus allowing for the formation of microenvironments conducive to cellular maturation and migration. The growth of cells in the presence of this support may be further enhanced by adding proteins, glycoproteins, glycosaminoglycans, a cellular matrix, and other materials to the support itself or by coating the support with these materials.

Similarly, tissue equivalents comprising a hydrated collagen lattice contracted by a contractile agent, such as fibroblast cells or blood platelets, in combination with a variety of cell types to form the tissue equivalent are disclosed in U.S. Pat. Nos. 4,485,096; 4,485,097; 4,539,716; 4,546,500; 4,604,346; and 4,835,102; 4,837,379; 5,256,418; 5,536,656; and RE 35,399, all of which are incorporated herein by reference.

In specific embodiments of the invention, bone marrow, bone, skin, dermis, liver, kidney, cartilage, ligament, tendon, pancreas, and heart valve tissues may be grown in the three dimensional culture system. The resulting cultures have a variety of applications ranging from transplantation or implantation, in vivo, of cells grown in the cultures, cytotoxicity testing and screening compounds in vitro, and the design of "bioreactors" for the production of biological materials in vitro. For example, skin tissue equivalents can be used as grafts to treat burn victims or ulcer patients, while kidney and liver tissue equivalents can be used for transplanting where disease has caused organ damage or failure. For diffuse tissues such as bone marrow, the proliferating cells could be isolated from the culture system for transplantation. Tendon, ligament, and cartilage tissue equivalents can be used for transplantation or prosthetics for seriously damaged tissue.

While the methods described above have met with some success, improved methods that accelerate the generation or improve the quality of tissue equivalents would be useful for more rapidly providing usable tissue equivalents. In particular, it would be useful to provide improved methods that promote more rapid acceleration of the cell type of interest and that accelerates the production of extracellular matrix by stromal cells in the tissue equivalent, and also improves the quality of the extracellular matrix produced.

SUMMARY OF THE INVENTION

The present invention provides methods that increase the production of tissue equivalents that are useful in transplantation therapy, drug testing, cytotoxicity testing of compounds, production of cellular compounds in quantity, and laboratory testing of tissue systems.

In one aspect, the present invention provides improved methods for accelerating the production of tissue equivalents by contacting the tissue equivalent with angiotensinogen, angiotensin I (AI), AI analogues, AI fragments and analogues thereof, angiotensin II ( AII), AII analogues, AII fragments or analogues thereof or AII $AT_2$ type 2 receptor agonists.

In another aspect of the present invention, an improved cell culture medium is provided for the production of tissue equivalents, wherein the improvement comprises addition to the culture medium of an effective amount of angiotensinogen, AI, AI analogues, AI fragments and analogues thereof, AII, AII analogues, AII fragments or analogues thereof or AII $AT_2$ type 2 receptor agonists.

In a further aspect, the present invention provides kits for the production of tissue equivalents, wherein the kits comprise an effective amount of angiotensinogen, AI, AI analogues, and/or AI fragments and analogues thereof, AII, AII analogues, AII fragments or analogues thereof, and/or AII $AT_2$ type 2 receptor agonists, and instructions for culturing the tissue equivalents.

DETAILED DESCRIPTION OF THE PREFERRED EMBODIMENTS

As defined herein, the term "tissue equivalents" refers to three-dimensional cell and tissue culture systems used for the long term proliferation of cells and tissues in vitro in an environment that more closely approximates that found in vivo. Such tissue equivalents include, but are not limited to, equivalents of epithelial tissue, connective tissue, cartilage, bone, organs, vascular grafts, bone marrow, skin, dermis, liver, kidney, cartilage, ligament, tendon, pancreas, heart valve tissues, glands and blood vessels and comprise living cells and extracellular matrix molecules, principally collagen, and may optionally be provided with components not typically found in normal tissue.

Unless otherwise indicated, the term "active agents" as used herein refers to the group of compounds comprising angiotensinogen, angiotensin I ( AI), AI analogues, AI fragments and analogues thereof, angiotensin II analogues, AII fragments or analogues thereof and AII $AT_2$ type 2 receptor agonists.

U.S. Pat. No. 5,015,629 to DiZerega (the entire disclosure of which is hereby incorporated by reference) describes a method for increasing the rate of healing of wound tissue, comprising the application to such tissue of angiotensin II ( AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (*Circulation Research* 60:786–790 (1987); Clouston et al., *Genomics* 2:240–248 (1988); Kageyama et al., *Biochemistry* 23:3603–3609; Ohkubo et al., *Proc. Natl. Acad. Sci.* 80:2196–2200 (1983); all references hereby incorporated in their entirety). The substance so formed is a decapeptide called angiotensin I (AI) which is converted to AII by the converting enzyme angiotensinase which removes the C-terminal His-Leu residues from AI [SEQ ID NO:37]. AII is a known pressor agent and is commercially available.

Studies have shown that AII increases mitogenesis and chemotaxis in cultured cells that are involved in wound repair, and also increases their release of growth factors and extracellular matrices (dizerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264:526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195:305–6 (1991). Additionally, AII and angiotensin III analogs and fragments thereof have been shown to be effective in tissue repair. (U.S. Pat. No. 5,629,292; International Application No. WO 95/08565; International Application WO 95/08337; International Application No. WO 96/39164; all references hereby incorporated in their entirety.)

Although AII has been shown to increase the proliferation of a number of cell types in vitro, it does not necessarily increase the proliferation of all cell types. AII has been shown to increase cellular proliferation in hair follicles in the area of a thermal injury. (Rodgers et al., J. Burn Care Rehabil. 18:381–388 (1997). The effect of AII on a given cell type has been hypothesized to be dependent, in part, upon the AII receptor subtypes the cell expresses (Shanugam et al., *Am. J. Physiol.* 268:F922–F930 (1995); Helin et al., *Annals of Medicine* 29:23–29 (1997); Bedecs et al., *Biochem J.* 325:449–454 (1997)). These studies have shown that AII receptor subtype expression is a dynamic process that changes during development, at least in some cell types (Id.)

While the preceding studies suggest that AII and other AII receptor agonists may accelerate wound repair through increased neovascularization, growth factor release, reepithelialization and/or production of extracellular matrix, the effect of angiotensinogen, AI, AI analogues, AI fragments and analogues thereof, AII, AII analogues, AII fragments or analogues thereof or AII $AT_2$ type 2 receptor agonists on accelerating the generation of tissue equivalents is unknown.

A peptide agonist selective for the AT2 receptor (AII has 100 times higher affinity for AT2 than AT1) has been identified. This peptide is p-aminophenylalanine6-AII ["(p-$NH_2$-Phe)6-AII)"], Asp-Arg-Val-Tyr-Ile-Xaa-Pro-Phe [SEQ ID NO.36] wherein Xaa is p-$NH_2$-Phe (Speth and Kim, *BBRC* 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., *BBRC* 187:1083–1090 (1992).

Many studies have focused upon AII(1–7) (AII residues 1–7) or other fragments of AII to evaluate their activity. AII(1–7) elicits some, but not the full range of effects elicited by AII. Pfeilschifter, et al., *Eur. J. Pharmacol.* 225:57–62 (1992); Jaiswal, et al., *Hypertension* 19(Supp. II):II-49-II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994).

As hereinafter defined, a preferred class of AT2 agonists for use in accordance with the present invention comprises AI, AI analogues, AI fragments and analogues thereof, AII, AII analogues or active fragments thereof having p-NH-Phe in a position corresponding to a position 6 of AII. In addition to peptide agents, various nonpeptidic agents (e.g., peptidomimetics) having the requisite AT2 agonist activity are further contemplated for use in accordance with the present invention.

The active AI, AI analogues, AI fragments and analogues thereof, AII analogues, fragments of AII and analogues thereof of particular interest in accordance with the present invention are characterized as comprising a sequence consisting of at least three contiguous amino acids of groups $R^1$–$R^8$ in the sequence of general formula I

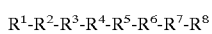

in which $R^1$ and $R^2$ together form a group of formula

wherein X is H or a one to three peptide group,
$R^A$ is suitably selected from Asp, Glu, Asn, Acpc (1-aminocyclopentane carboxylic acid), Ala, Me²Gly, Pro, Bet, Glu(NH₂), Gly, Asp(NH₂) and Suc, $R^B$ is suitably selected from Arg, Lys, Ala, Orn, Ser(Ac), Sar, D-Arg and D-Lys;

$R^3$ is selected from the group consisting of Val, Ala, Leu, Lys, norLeu, Ile, Gly, Pro, Aib, Acpc and Tyr;

$R^4$ is selected from the group consisting of Tyr, Tyr(PO₃)₂, Thr, Ser, Ala, homoSer and azaTyr;

$R^5$ is selected from the group consisting of Ile, Ala, Leu, norLeu, Val and Gly;

$R^6$ is His, Arg or 6-NH₂-Phe;

$R^7$ is Pro or Ala; and $R^8$ is selected from the group consisting of Phe, Phe(Br), Ile and Tyr, excluding sequences including $R^4$ as a terminal Tyr group.

Compounds falling within the category of AT2 agonists useful in the practice of the invention include the AII analogues set forth above subject to the restriction that $R^6$ is p-NH₂-Phe.

Particularly preferred combinations for $R^A$ and $R^B$ are Asp-Arg, Asp-Lys, Glu-Arg and Glu-Lys. Particularly preferred embodiments of this class include the following: AII, AIII or AII(2–8), Arg-Val-Tyr-Ile-His-Pro-Phe [SEQ ID NO:2]; AII(3–8), also known as des1-AIII or AIV, Val-Tyr-Ile-His-Pro-Phe [SEQ ID NO:3]; AII(1–7), Asp-Arg-Val-Tyr-Ile-His-Pro {SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII (1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII(4–8), Tyr-Ile-His-Pro-Phe [SEQ ID NO:15] were also tested and found not to be effective.

In a particularly preferred embodiment, the active compounds of the present invention are selected from those comprising the following general formula:

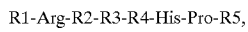

wherein R1 is selected from the group consisting of H, Gly and Asp;

R2 is selected from the group consisting of Val, Pro, and Acpc;

R3 is selected from the group consisting of Tyr and Tyr(PO₃)₂;

R4 is selected from the group consisting of Ala, Val, Ile, Leu, and norLeu; and

R5 is Phe, Ile, or is absent.

Another class of compounds of particular interest in accordance with the present invention are those of the general formula II

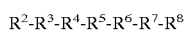

in which $R^2$ is selected from the group consisting of H, Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO₃)₂, Thr, Ser, homoSer and azaTyr;

$R^5$ is selected from the group consisting of Ile, Ala, Leu, norLeu, Val and Gly;

$R^6$ is His, Arg or 6-NH₂-Phe;

$R^7$ is Pro or Ala; and $R^8$ is selected from the group consisting of Phe, Phe(Br), Ile and Tyr.

A particularly preferred subclass of the compounds of general formula II has the formula

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

| Abbreviation for Amino Acids | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity: Hydrophobic side chains in positions $R^3$, $R^6$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr. Furthermore, Lys has surprisingly been found to be suitable at $R^3$ (see Examples).

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. Furthermore, Ala has surprisingly been found to be suitable at the $R^4$ position (See Examples). In this position, Tyr is particularly preferred as it may form a hydrogen bond with the receptor site capable of accepting a hydrogen from the phenolic hydroxyl (Regoli, et al. (1974), supra).

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the AI, AI analogues, AI fragments and analogues thereof, AII analogues, fragments and analogues of fragments of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

In one aspect of the present invention, a method of accelerating the production of tissue equivalents by exposure to angiotensinogen, AI, AI analogues, AI fragments and analogues thereof, AII analogues, AII fragments or analogues thereof or AII $AT_2$ type 2 receptor agonists (the "active agents") is disclosed. Experimental conditions for the production of various tissue equivalents have been reported as follows: liver tissue equivalents (U.S. Pat. No. 5,624,840), bone marrow tissue equivalents (U.S. Pat. No. 5,541,107), ligament tissue equivalents (U.S. Pat. No. 5,521,087), kidney tissue equivalents (U.S. Pat. No. 5,516,680), blood vessel tissue equivalents (U.S. Pat. No. 5,256,418), vascular graft equivalents (U.S. Pat. No. 5,628,781 and 5,387,236) and skin tissue equivalents (5,512,475, 4,835,102, and RE 35,399), all references herein incorporated by reference in their entirety.

In one embodiment, tissue equivalents are prepared according to standard methods (U.S. Pat. Nos. 5,624,840, 5,541,107, 5,521,087, 5,516,680, 5,256,418, 5,512,475, 4,835,102, and RE 35,399) and incubated in the presence of,

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr($PO_3)_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by methods such as those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. The disclosures of the foregoing treatises are incorporated by reference herein.

In general, these methods involve the sequential addition of protected amino acids to a growing peptide chain (U.S.

preferably, between about 0.1 ng/ml and about 1 mg/ml of the active agents of the invention.

In another embodiment, a dermal equivalent is formed by the inoculation of fibroblasts onto a three-dimensional matrix and their growth to subconfluence (U.S. Pat. No. 5,578,485, incorporated by reference herein in its entirety). The three-dimensional support may be of any material and/or shape that: (a) allows cells to attach to it (or can be modified to allow cells to attach to it); and (b) allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton, polyglycolic acid (PGA), cat gut sutures, cellulose, gelatin, dextran, etc. Any of these materials may be woven into a mesh, for example, to form the three-dimensional matrix. Certain materials, such as nylon, polystyrene, etc., are poor substrates for cellular attachment. When these materials are used as the three-dimensional support matrix, it is advisable to pre-treat the matrix prior to inoculation of stromal cells in order to enhance the attachment of stromal cells to the matrix. For example, prior to inoculation with stromal cells, nylon matrices could be treated with 0.1M acetic acid, and incubated in polylysine, FBS, and/or collagen to coat the nylon. Polystyrene could be similarly treated using sulfuric acid.

Where the three-dimensional culture is itself to be implanted in vivo, it may be preferable to use biodegradable matrices such as poly glycolic acid, catgut suture material, or gelatin, for example (U.S. Pat. No. 5,578,485). Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 210 mu m and an average nylon fiber diameter of 90 mu m (#3-210/36, Tetko, Inc., N.Y.).

In a preferred embodiment, the fibroblasts are allowed to proliferate until the entire growth substrate is covered, although only approximately 60% confluency of the fibroblasts on the three-dimensional matrix is required to support the growth of epidermal cells later inoculated. The fibroblasts will continue to divide even after they have reached confluency because the three-dimensional culture permits the exit of cells, thereby preventing contact inhibition. Although any fibroblasts may be utilized in the inoculum, it is advantageous to use skin fibroblasts, as these will deposit the appropriate types of collagen and elaborate other dermal components. Fibroblasts may be allogeneic or autologous. Skin fibroblasts may be readily obtained from cellular suspensions prepared by mechanical and/or enzymatic disaggregation of dermal tissue. When the cellular suspension obtained is plated, the fibroblasts will adhere more quickly than other cells, and thus, can be grown to confluence, lifted by mild enzymatic treatment and inoculated onto the three-dimensional matrix.

While the use of fibroblasts alone is sufficient to form a three-dimensional stromal matrix that functions as a dermal equivalent, additional types of stromal cells may be used to inoculate the three-dimensional matrix. These include, but are not limited to endothelial cells, pericytes, macrophages, monocytes, lymphocytes, plasma cells, adipocytes, etc.

In a further preferred embodiment, epidermal cells are inoculated onto the dermal equivalent to provide full thickness skin equivalents (U.S. Pat. No. 5,578,485, incorporated by reference herein in its entirety). To this end, melanocytes and keratinocytes may be inoculated simultaneously, or preferably, in sequence. For example, keratinocytes can be inoculated onto subconfluent melanocytes which were previously inoculated onto the stromal matrix.

Melanocytes and keratinocytes may be allogeneic or autologous in their relationship to fibroblast stromal cells, can be isolated from skin using known procedures which involve incubating skin in a digestive enzyme, such as trypsin, in order to separate dermal and epidermal layers.

In one embodiment, keratinocytes and melanocytes may be isolated as follows. A tissue sample, e.g. foreskin, may be trimmed so that the entire surface may be easily exposed to antibiotics. Tissue may be first washed in a concentrated antibiotic solution for twenty minutes, followed by two subsequent washes of ten minutes each. The outer portion of the tissue may then be cut into small pieces, and then placed in a 0.15% trypsin solution (in PBS without calcium or magnesium), quickly removed, placed in a fresh container of the same trypsin solution (such that all the tissue is covered by solution), and refrigerated overnight at between about 2° C. and 8° C. The next day, the tissue pieces may be removed from the trypsin solution, and the epidermis separated from the dermis using curved forceps. The epidermis may be placed in a conical tube, and about 0.15% trypsin in PBS (without calcium or magnesium) may be used to digest the tissue into a single cell suspension; to facilitate this process, the sample may be repeatedly aspirated into and out of a Pasteur pipette. When the sample appears to be a single cell suspension, it may be centrifuged at 1400 g for about 7 minutes and then resuspended in either growth media or in growth media containing 0.01 mg/ml PMA, which selects for melanocytes. Accordingly, cultures of keratinocytes or melanocytes may be produced. The epidermal cells can be suspended and used to inoculate the dermal equivalent. Alternatively, the epidermal cell suspension can be plated and melanocytes and keratinocytes separated based upon their differential attachment qualities. Isolated melanocytes may first be inoculated onto the dermal equivalent and allowed to grow for a few days prior to inoculation of keratinocytes. This "tissue" grows rapidly and can be maintained in nutrient media without exogenous growth factors.

In a preferred embodiment, a dermal equivalent produced as set forth supra may be inoculated with keratinocytes as follows (U.S. Pat. No. 5,478,739, incorporated by reference herein in its entirety). Fresh dermal equivalent cultures, or dermal equivalent cultures removed from the freezer and rinsed with PBS in order to remove dimethyl sulfoxide (DMSO), may be allowed to equilibrate in stratification medium (DMEM with 5 percent fetal bovine serum; 100 mu g/ml ascorbate (Sigma) and 0.5 mu g/ml hydrocortisone (Sigma)) for about 24–48 hours. Keratinocytes may then be seeded onto the dermal equivalent at a density of about $5 \times 10^5$ keratinocytes per $cm^2$ of dermal equivalent. The keratinocyte/dermal equivalent co-cultures may then be incubated submerged in stratification medium for 5–7 days, then raised such that keratinocytes may differentiate at the air/liquid interface. After about 12–14 days in culture, a cholesterol-rich lipid supplement (Sigma) (0.5%) may be added to the stratification medium and the cultures may be grown for an additional 12–21 days until a multi-layered stratum corneum is formed.

In another embodiment, bone marrow cells are grown on a three-dimensional support in co-cultures with stromal cells comprising fibroblasts (of either fetal or bone marrow origin) or a mixture of cell types which comprise the stromal components of normal marrow, including fibroblasts, macrophages, reticular cells, and adipocytes (U.S. Pat. No. 5,541,107). Factors derived from media of splenic and/or hepatic (liver) macrophage cultures or from subsets of stromal cells may optionally be added to the culture. The three-dimensional culture system of the present invention appears to maximize the proliferation of multipotential hematopoietic stem cells which have the capability of repopulating bone marrow when the bone marrow has been destroyed by intrinsically or environmentally-mediated disease or by the treatment of such disease with chemotherapy and/or radiation.

Alternatively, a liver tissue equivalent is produced by inoculation and culturing of liver parenchymal cells on a pre-established three-dimensional stromal tissue (U.S. Pat. No. 5,624,840). The stromal tissue comprises stromal cells grown on a three-dimensional matrix or framework. The stromal cells comprise fibroblasts with or without additional cells and/or elements. The fibroblasts and other cells and/or elements that comprise the stroma may be fetal or adult in origin, and may be derived from convenient sources such as skin, liver, pancreas, etc. Such tissues and/or organs can be obtained by appropriate biopsy or upon autopsy. In fact, cadaver organs may be used to provide a generous supply of stromal cells and elements.

In another embodiment, bone, ligament, cartilage and tendon equivalents, are produced by forming a collagen gel having living connective tissue cells dispersed therein (U.S. Pat. No. 5,521,087). The cells are capable of contracting the gel. The gel is maintained under conditions suitable for contraction by the connective tissue cells, while simultaneous contraction of the gel is restrained to define an axis of predetermined length for cell alignment. The connective tissue cells align along the defined axis to produce an oriented tissue-equivalent having increased mechanical strength in the direction of the axis.

In another embodiment, kidney tissue equivalents are prepared by culturing kidney parenchymal cells cultured on a living stromal tissue prepared in vitro, said living stromal tissue comprising stromal cells and connective tissue proteins naturally secreted by the stromal cells attached to and substantially enveloping a framework composed of a biocompatible, non-living material formed into a three-dimensional structure having interstitial spaces bridged by the stromal cells (U.S. Pat. No. 5,516,680).

In another embodiment, pancreatic tissue equivalents are formed by mincing pancreatic tissue and washing in calcium-free, magnesium-free buffer (U.S. Pat. No. 5,578,485, incorporated by reference herein in its entirety.) The minced tissue fragments are incubated in a solution of trypsin and collagenase. Dissociated cells may be filtered using a 20 mu m nylon mesh, resuspended in a suitable buffer such as Hanks balanced salt solution, and pelleted by centrifugation. The resulting pellet of cells can be resuspended in minimal amounts of appropriate media and inoculated onto the three-dimensional stroma.

In another embodiment, living vascular graft equivalents, comprising a polymeric backbone and endothelial cells are prepared as described in U.S. Pat. Nos. 5,628,781 and 5,387,236, both references hereby incorporated in their entirety. In a preferred embodiment, a polymeric substrate for the vascular prosthesis is dispersed in a solution of biological tissue fragments such as vascular tissues, connective tissues, fat tissues and muscular tissues and/or cells such as vascular endothelial cells, smooth muscle cells and fibroblast cells. (U.S. Pat. No. 5,387,236) The cells and/or tissue fragments are deposited and captured within the wall and on the inner surface of the vascular prosthesis substrate wall from the outside and/or the inside of the vascular prosthesis substrate by providing a pressure differential between the outside and the inside of the substrate. The interior space of the vascular prosthesis can be vacuumized or pressurized, and the cells and/or tissue fragments are deposited and captured in and on the walls either outside or inside of the prosthesis substrate. In a preferred embodiment, the living vascular graft further comprises vascular smooth muscle cells and fibroblasts.

Methods for producing heart valve equivalents are described in U.S. Pat. Nos. 5,713,950; 5,480,424; 5,192,312; and 5,052,934, all references herein incorporated by reference in their entirety.

In order to accelerate the generation of the all of the above tissue equivalents, they are exposed to preferably, between about 0.1 ng/ml and about 1 mg/ml of the active agents of the invention as described above. Acceleration of tissue equivalent generation by exposure to the active agents occurs via increased proliferation of the cells that comprise the tissue equivalent, increase in growth factor production by cells of the tissue equivalent, and via increasing production of extracellular matrix components by stromal cells within the tissue equivalents.

Proliferation of cells in the tissue equivalent can be quantitated using any one of a variety of techniques well known in the art, including, but not limited to, bromodeoxyuridine incorporation (Vicario-Abejon et al., 1995), $^3$H-thymidine incorporation (Fredericksen et al., 1988), or antibody labeling of a protein present in higher concentration in proliferating cells than in non-proliferating cells. In a preferred embodiment, accelerated production of tissue equivalents is assessed by antibody detection of a protein known to be present in higher concentrations in proliferating cells than in non-proliferating cells, including but not limited to proliferating cell nuclear antigen (PCNA, or cyclin; Zymed Laboratories, South San Francisco, Calif.).

Increased production of growth factors, including but not limited to transforming growth factor beta, fibroblast growth factor, and epidermal growth factor, by cells of the tissue equivalent can be quantitated by standard immunohistochemical techniques using antibodies to the growth factors (DAKO, Carpemterica, Calif.; Genzyme, Cambridge, Mass.; Sigma Chemical Co., St. Louis, Mo.).

Increasing production of extracellular matrix components by the stromal component of the tissue equivalent can be quantitated by antibody labeling of extracellular matrix components, including but not limited to fibronectin, elastin, glycosaminoglycans, and laminin (DAKO, Carpemterica, Calif.; Pharmingen, San Diego, Calif.).

In another aspect of the present invention, an improved cell culture medium is provided for accelerated production of tissue equivalents, wherein the improvement comprises addition to the cell culture medium of an effective amount of active agents, as described above. For any given active agent, the optimum concentration for a given formulation may be readily determined empirically. In general, a concentration of active agent suitable for use in accordance with the present invention preferably ranges between about 0.1 ng/ml and about 1 mg/ml active agents.

Any cell culture media that can support the growth of tissue equivalents can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof. In a preferred embodiment, the defined cell culture medium described in U.S. Pat. No. 5,712,163 is used.

The improved cell culture medium can be supplied in either a concentrated (ie: 10×) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.).

In a further aspect, the present invention provides kits for the propagation of tissue equivalents, wherein the kits comprise an effective amount of the active agents of the invention, and instructions for their use in accelerating the production of tissue equivalents.

In a preferred embodiment, the kit further comprises cell culture growth medium. Any cell culture media that can support the growth of tissue equivalents can be used with the present invention. Examples of such cell culture media are described above.

The improved cell culture medium can be supplied in either a concentrated (ie: 10x) or non-concentrated form, and may be supplied as a liquid, a powder, or a lyophilizate. The cell culture may be either chemically defined, or may contain a serum supplement. In a further embodiment, the kit further comprises a three-dimensional support material.

EXAMPLE 1

Effect of AII on Epidermal Layer Thickness

The purpose of this study was to determine, by quantitative histology, the effect of presoaking a living skin equivalent (LSE) in a lactated Ringer's solution (LRS)-Dextrose containing AII, on the thickness of the epidermis on day 23 post-grafting.

Twenty three male Swiss nude mice (22–24 grams) were purchased from Taconic Laboratories and quarantined at least two days prior to surgery, and divided into 4 groups of mice. The mice were anesthetized with an intramuscular injection of Ketamine (ketaset; Phoenix Pharmaceuticals, Inc.) and Rompun (xylazine; Phoenix Pharmaceuticals, Inc.) and a 1 cm×1 cm full thickness skin excision was made on their dorsal surface. Each group received an Apligraph LSE (Organogenesis; Canton, Mass.) that had been soaked for 10 minutes in concentrations of AII ranging from 0 to 1.0 mg/ml. The LSE was placed in the defect and trimmed with microscissors so that no gap was observed between the edges of the mouse skin and the LSE. After the graft was placed, the dorsal surface of the mouse was covered by petroleum embedded gauze (Dermacea) followed by two adhesive bandages (Baxter). After recovery from anesthesia, the mice were returned to their individual cages and observed daily until euthenasia. The mice received intramuscular analgesia for the first three days after surgery. No mouse lost their bandage prior to bandage removal on day 7 and day 23. At necropsy, the degree of graft taken and the appearance of the grafted tissue was noted prior to placement of the biopsy in 10% buffered formalin in preparation for paraffin embedding and sectioning for hematoxylin and eosin staining.

All grafts appeared healthy (except one control which had lost its graft) and inosculation was noted for 80–100% of the graft edges. On day 7, one of the AII-treated grafts had numerous vessels attached to its underside (against the fascia of the nude mice after full thickness excision). This was not noted on any of the other mice.

Measurement of the thickness of the epidermis at day 23 was accomplished with an ocular micrometer in a 10×ocular at the 10×magnification on the objective (100×total magnification). The thickest part of each graft was measured and the thickness of the graft at one-half of a 10×field to each side of the thickest portion was also measured. The epidermal thickness increased in a concentration-dependent manner after AII administration.

EXAMPLE 2

Effect of AII on the Outgrowth of Keratinocytes from Explants of Human Skin

Human skin explants were obtained from surgery of split thickness skin grafts and cut by scalpel in to 2 mm×2 mm squares. Ten explants per condition were placed dermal side down on frozen and thawed Dermagraft (Advanced Tissue Sciences, San Diego, Calif.) and cultured at the air-liquid interface using Keratinocyte-SFM medium (Gibco BRL, Grand Island, N.Y.) supplemented with epidermal growth factor and bovine pituitary extract according to the manufacturer's instructions. The culture medium contained penicillin (50 U/ml) and streptomycin (50 µg/ml) and extra calcium chloride to a final concentration of 1 mM. Angiotensin II was added to the culture medium at a final concentration of 1 or 10 µg/ml. The cultures were maintained at 37° C. with 5% $CO_2$ and medium with and without AII and the medium was changed twice weekly. After 7 days, the cultures were fixed in formalin for one hour, stained with hematoxylin and washed in tap water. The dermal replacements appeared dark purple except for the area where the keratinocytes exclude the stain. Cultures were photographed using a dissection microscope at a fixed magnification and the area of outgrowth was quantified by gravimetric planimetry. Exposure to AII during the outgrowth period increased the area of the artificial dermis covered with keratinocytes.

EXAMPLE 3

Contraction of Collagen Lattices by Human Fibroblasts

Contraction of collagen lattices is a first step in the preparation of an artificial dermis, where keratinocytes are subsequently grown in the collagen matrix. Collagen lattices can also be implanted sub-cutaneously and used as a bulking-up agent for plastic surgery applications.

Normal human fibroblasts were purchased from Clonetics (San Diego, Calif.) and were thawed and cultured in Fibroblast Growth Medium (Clonetics) according to the manufacturer's instructions. Once the cells reached confluence in the flask, they were harvested by trypsinization and utilized for the studies described below.

Rat tails were harvested from 200 gram female rats and frozen until use. The frozen rat tails were thawed in 70% (vol/vol) ethanol for 20 minutes. The tendon bundles were excised in 70% ethanol in a vertical laminar flow hood. The individual tendons were pulled out of the tendon sheath, minced, and placed in dilute acetic acid (1:1000) using 250 ml per tail. The mixture was incubated at 4° C. for 48 hours, at which point the minced tendons had swelled to the volume of the dilute acetic acid. The viscous mixture was centrifuged at 23,000 rpm in a Beckman L ultracentrifuge for 1 hour. The supernatant was harvested and further refined. This crude collagen solution was mixed with 0.1M NaOH in a 6:1 ratio to neutralize the acetic acid and precipitate the collagen. The mixture was then centrifuged at 1500 rpm for 5 minutes. The supernatant was discarded and an equal volume of fresh acetic acid (1:1000) was introduced to resolubilize the collagen over 48 hours. This solution was stored at 4° C. as refined collagen. The protein concentration was determined by BCA assay.

The collagen lattices for the assessment of contraction by fibroblasts and angiotensin II were formed in 60 mm Falcon bacteriological dishes. Each dish contained 1 ml 4×DMEM High glucose medium, 1 ml fetal calf serum, 0.25 ml NaOH, 1.5 ml of 500 µg/ml refined collagen and 1 ml of fibroblasts in Fibroblast Growth Medium ($7.5 \times 10^4$ cells/ml to $7.5 \times 10^5$ cells/ml). In these cultures, various concentrations of AII (1 to 10 µg/ml) were added to assess the effect of AII on the formation of an artificial dermis. The cultures were placed in an incubator at 37° C. in an atmosphere of 5% $CO_2$ in air.

At various times after culture initiation, the diameter of the formed lattice was measured. As there are slight differences in diameter at various points (ie: the lattices were not always perfectly round), the average of the largest and the smallest diameters were taken. AII accelerated the contraction of collagen lattices.

Similar experiments were conducted using AII analogues and fragments, except that ten μg/ml of each of the peptides shown in Table 3 were added to 1×10⁵ of fibroblasts/well. At various times after culture initiation, the diameter of the formed lattice was measured. The results of these experiments are shown in Table 4, and demonstrate that each of the AII analogues and fragments accelerated the contraction of collagen lattices.

TABLE 3

Designation for Analogues/Fragments

| Abbreviation | Sequence | SEQ ID NO: |
|---|---|---|
| Gly$^1$-AII | GRVYIHPF | SEQ ID NO:39 |
| NorLeu$^4$-AIII | --RVYnLHPF | SEQ ID NO:40 |
| Acpc$^3$-AII | DR(Acpc)YIHPF | SEQ ID NO:41 |
| Ile$^8$ AII | DRVYIHPI | SEQ ID NO:38 |
| Ala$^4$-AIII | --RVYAHPF | SEQ ID NO:18 |
| AII(1–7) | DRVYIHP-- | SEQ ID NO:4 |
| AII | DRVYIHPF | SEQ ID NO.1 |

TABLE 4

Results of Collagen Lattice Contraction with AII Analogues and Fragments

| | Day of Culture Diameter of Lattice (cm) | | | |
|---|---|---|---|---|
| Peptide | Day 1 | Day 2 | Day 3 | Day 4 |
| None | 3.5 | 2.8 | 2.3 | 1.9 |
| Ala4-AIII | 3.4 | 2.7 | 1.9 | 1.6 |
| Gly1 AII | 3.4 | 2.2 | 1.6 | 1.5 |
| NorLeu4 AIII | 3.4 | 2.0 | 1.6 | 1.5 |
| Acpc3 AII | 3.5 | 2.0 | 1.6 | 1.4 |
| AII(1–7) | 3.4 | 2.4 | 2.0 | 1.7 |
| AII | 3.3 | 2.4 | 1.6 | 1.4 |
| Ile8 AII | 3.4 | 2.4 | 1.7 | 1.4 |

Integra, a commercially available artificial dermis of chondrotin sulfate and collagen, was obtained (Integra Life Sciences) and used in culture as a matrix for keratinocyte growth. The Integras was washed free of preservative by a sterile saline for injection and cut to size to fit snugly into the bottom of 24 well plates. After trimming, the pieces of Integra were placed silicone-side down into the wells.

Human keratinocytes were purchased from Clonetics and thawed and cultured as described in Example 3, except that they were grown in Keratinocyte Growth Medium, as per the manufacturer's instructions. Once the cells reached confluence in the flask, they were detached from the tissue culture flasks by trypsinization. The cells were resuspended at 1×10⁵ cells/ml in Keratinocyte Growth Medium or Keratinocyte Basal Medium with or without 10 μg/ml of various AII-related peptides (AII, AII(1–7), Pro3 AII(1–7), Ala4-AIII, and Pro3-AII; see Table 5 below). One ml of these cell preparations was added to wells of the 24 well plates containing Integra membrane. The cultures were placed in an incubator at 37° C. in an atmosphere of 5% $CO_2$ in air. At various times after initiation of the cultures, the number of keratinocytes on the surface of the Integra membrane in 5 100×fields was assessed under phase contrast microscopy. The data and demonstrate that each of the peptides tested increased the proliferation of keratinocytes on this artificial membrane.

TABLE 5

Designation for Analogues/Fragments

| Name | Abbreviation | Sequence | SEQ ID NO: |
|---|---|---|---|
| GSD 24B | Pro$^3$-AII | DRPYIHPF | SEQ ID NO:31 |
| 2GD | Pro$^3$-AII(1–7) | DRPYIHP | SEQ ID NO:42 |
| GSD 22A | Ala$^4$-AIII | RVYAHPF | SEQ ID NO:18 |
| AII(1–7) | | DRVYIHP-- | SEQ ID NO:4 |
| AII | | DRVYIHPF | SEQ ID NO.1 |

The present invention, by providing a method for enhanced production of tissue equivalents, will greatly increase the clinical benefits of tissue equivalent transplantation, as well as increasing the utility of drug and cytotoxicity testing on tissue equivalents, production of cellular compounds in quantity, and laboratory testing of tissue equivalent systems.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

We claim

1. A method for accelerating the production of a tissue equivalent comprising contacting the tissue equivalent with an amount effective to accelerate generation of tissue equivalents of at least one active agent comprising a sequence of at least three contiguous amino acids of groups $R^1$-$R^8$ in the sequence of general formula I $$R^1\text{-}R^2\text{-}R^3\text{-}R^4\text{-}R^5\text{-}R^6\text{-}R^7\text{-}R^8$$

wherein $R^1$ is selected from the group consisting of Asp, Glu, Asn, Acpc, Ala, Me 2Gly, Pro, Bet, Glu($NH_2$), Gly, Asp($NH_2$) and Suc;

$R^2$ is selected from the group consisting of Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc, Lys and Tyr;

$R^4$ is selected from the group consisting of Tyr, Tyr($PO_3$)$_2$, Thr, Ser, Ala, homoSer and azaTyr;

$R^5$ is selected from the group consisting of Ile, Ala, Leu, norLeu, Val and Gly;

$R^6$ is selected from the group consisting of His, Arg and 6-$NH_2$-Phe;

$R^7$ is selected from the group consisting of Pro and Ala; and $R^8$ is selected from the group consisting of Phe, Phe(Br), Ile and Tyr, excluding sequences including $R^4$ as a terminal Tyr group.

2. The method of claim 1 wherein the active agent complises a sequence of SEQ ID NO:4.

3. The method of claim 1 wherein the concentration of active agent is between 0.1 ng/mL and 1.0 mg/mL.

4. The method of claim 1 where the tissue equivalent is selected from the group consisting of a skin, dermis, bone, bone marrow, pancreas, heart valve, vascular graft, cartilage, ligament, liver, and kidney tissue equivalent.

5. The method of claim 1, wherein the active agent comprises at least four contiguous amino acid residues of the general formula I.

6. The method of claim 1, wherein the active agent comprises at least five contiguous amino acid residues of the general formula I.

7. The method of claim 1, wherein the active agent comprises at least six contiguous amino acid residues of the general formula I.

8. The method of claim 1, wherein the active agent comprises at least seven contiguous amino acid residues of the general formula I.

9. The method of claim 1, wherein the active agent consists of at least three contiguous amino acid residues of the general formula I.

10. The method of claim 1, wherein the active agent consists of at least four contiguous amino acid residues of the general formula I.

11. The method of claim 1, wherein the active agent consists of at least five contiguous amino acid residues of the general formula I.

12. The method of claim 1, wherein the active agent consists of at least six contiguous amino acid residues of the general formula I.

13. The method of claim 1, wherein the active agent consists of at least seven contiguous amino acid residues of the general formula I.

14. The method of claim 1, wherein the active agent consists of a sequence of SEQ ID NO:4.

15. A method for accelerating the production of a tissue equivalent comprising contacting the tissue equivalent with an amount effective to accelerate generation of tissue equivalents of at least one active agent comprising a sequence of the following general formula II:

$$R^1\text{-Arg-}R^2\text{-}R^3\text{-}R^4\text{-His-Pro-}R^5$$

wherein $R^1$ is selected from the group consisting of H, Gly and Asp;

$R^2$ is selected from the group consisting of Val Pro, and Acpc;

$R^3$ is selected from the group consisting of Tyr and Tyr(PO$_3$)$_2$;

$R^4$ is selected from the group consisting of Ala, Val, Ile, Leu, and norLeu; and $R^5$ is selected from the group consisting of Phe$_2$ Ile, or is absent.

16. The method of claim 15 wherein the active agent comprises a sequence of SEQ ID NO:4.

17. The method of claim 15 wherein the concentration of active agent is between 0.1 ng/mL and 1.0 mg/mL.

18. The method of claim 15 where the tissue equivalent is selected from the group consisting of a skin, dermis, bone, bone marrow, pancreas, heart valve, vascular graft, cartilage, ligament, collagen lattice, liver, and kidney tissue equivalent.

19. The method of claim 15 where the tissue equivalent is selected from the group consisting of a collagen lattice and dermis tissue equivalent.

20. The method of claim 15, wherein the active agent consists of a sequence of general formula II.

21. The method of claim 15, wherein the active agent does not consist of angiotensin II (SEQ ID NO:1).

22. The method of claim 15, wherein the active agent consists of a sequence of SEQ ID NO:4.

* * * * *